United States Patent [19]

Riva et al.

[11] 4,275,061

[45] Jun. 23, 1981

[54] STEROIDS AND PROCESS FOR PREPARING THE SAME

[75] Inventors: Mario Riva, Monza; Luciano Toscano, Milan, both of Italy

[73] Assignee: Pierrel S.p.A., Milan, Italy

[21] Appl. No.: 24,460

[22] Filed: Mar. 27, 1979

Related U.S. Application Data

[63] Continuation of Ser. No. 839,881, Oct. 6, 1977, abandoned, which is a continuation of Ser. No. 596,266, Jul. 16, 1975, abandoned.

[30] Foreign Application Priority Data

Jun. 14, 1975 [GB] United Kingdom ............... 25478/75

[51] Int. Cl.$^3$ ............................................ A61K 31/56

[52] U.S. Cl. ............................. 424/243; 260/397.45; 260/239.55 D

[58] Field of Search .................. 260/239.55 D, 397.45

[56] References Cited

U.S. PATENT DOCUMENTS

| 3,652,554 | 3/1972 | Anner et al. | 260/239.55 |
| 4,076,737 | 2/1978 | Anner et al. | 260/397.45 |

*Primary Examiner*—Elbert L. Roberts
*Attorney, Agent, or Firm*—Bacon & Thomas

[57] ABSTRACT

The present invention relates to 2-chloro-6β-fluoro-pregna-1,4-diene-3,20-diones having good anti-inflammatory activity, to processes for their preparation and pharmaceutical compositions thereof.

23 Claims, No Drawings

STEROIDS AND PROCESS FOR PREPARING THE SAME

This is a continuation, of application Ser. No. 839,881, filed Oct. 6, 1977, now abandoned, which is in turn a continuation of Application Ser. No. 596,266, filed July 16, 1975, now abandoned.

The present invention relates to a new class of steroids having good anti-inflammatory activity, to processes of making them and to pharmaceutical compositions containing them.

Many steroids having anti-inflammatory activity upon topical and/or systemic administration are known and some of them have quite satisfactory anti-inflammatory activity.

Unfortunately they all tend to give undesired side effects. For instance they may disturb the mineral balance in the subject to which they are administered, for example they may reduce the potassium and/or sodium balance and they may affect adversely the adrenals function.

Accordingly their application has to be conducted with caution. It has been our object to produce novel steroids that have very good anti-inflammatory activity, preferably higher than that of most or all known steroids, and which have very low or no side effects, preferably when measured in absolute terms but in particular when measured as the therapeutic ratio, i.e. the ratio of the active dose that is required to achieve the desired anti-inflammatory activity to the minimum dose that incurs undesired side effects.

We have now found that 2-chloro-6$\beta$-fluoro-pregna-1,4-diene-3,20-diones have high anti-inflammatory activity and at same time avoid completely or at least minimise the undesirable side effects of known steroid compound.

The preferred novel compounds of the invention have the general formula

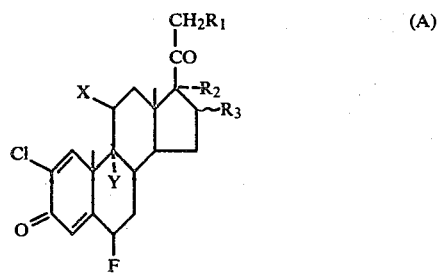

(A)

wherein
X represents Br, Cl, or OQ;
Y represents Br, Cl, F or H;
$R_1$ represents OQ;
$R_2$ represents OQ;
$R_3$ represents H, $\alpha$OQ, $\alpha CH_3$ or $\beta CH_3$;
and the radicals Q, which may be the same or different, are selected from H and acyl radicals, or the groups OQ in the 16 and 17 positions or in the 17 and 21 positions may together form a cyclic ketal, cyclic acetal or cyclic alkyl orthoester, and pharmaceutically acceptable salts or esters with those compounds wherein at least one radical Q is a polycarboxylic or an inorganic acid radical.

The salts are preferably water soluble and are preferably with an alkali metal, for example sodium or potassium. The esters are preferably with an aliphatic, aryl, arylaliphatic or cycloaliphatic group.

The OQ group of $R_1$ can be also an alkyl orthoester.

Typical values of aliphatic radicals suitable as the esterifying radical in a dicarboxylic acyl group are alkyl, preferably containing up to 7 carbon atoms and alkenyl. Particularly preferred are alkyl containing up to 4 carbon atoms, especially methyl, ethyl and propyl. Typical cycloaliphatic are cycloalkyl radicals containing 5 to 8 carbon atoms, for example cyclopentyl and cyclohexyl.

Typical arylaliphatic radicals are phenyl alkyl radicals, for example where alkyl is as described above, for instance benzyl. Typical aryl radicals are those containing a phenyl ring, for example unsubstituted phenyl.

When Q is acyl, OQ thus being an ester radical, Q may be the radical of an inorganic acid, for example sulphuric acid or phosphoric acid, or an organic acid, for example a sulphonic acid or a carboxylic acid, including aliphatic, alicyclic, aromatic, arylaliphatic and heterocyclic carboxylic acids, including carboxylic acids such as thiocarboxylic acids and amino carboxylic acids. Preferred carboxylic acids are formic acid, acetic acid, chloroacetic acid, trifluoroacetic acid, propionic acid, butyric acid, valeric acid, trimethylacetic acid, diethylacetic acid, caproic acid, crotonic acid, enanthic acid, caprylic acid, capric acid, palmitic acid, undecanic acid, undecylenic acid, oxalic acid, succinic acid, glutaric acid, pimelic acid, tartaric acid, maleic acid, lactic acid, carbamic acid, glycine, alkoxy carboxylic acids, hexahydrobenzoic acid, cyclopentylpropionic acids, cyclohexylacetic acid, cyclohexylbutyric acids, benzoic acid, phthalic acid, phenylacetic acid, phenylpropionic acids, furane-2-carboxylic acid, nicotinic acid and isonicotinic acid.

Preferred sulphonic acids are methanesulphonic acid and toluenesulphonic acid.

Particularly preferred acyl radicals are those derived from acetic acid, trimethylacetic acid, propionic acid, $\beta$-phenyl-propionic acid, $\alpha$-phenylpropionic acid, valeric acid and dicarboxylic acids, for example succinic acid.

It is often preferred that in $R_1$ Q shall be an acyl group as described above, particularly the preferred carboxylic acyl groups as described above, since 21-esters have particularly good biological activity. It is often preferred that when X represents OQ, Q shall be hydrogen. Any convenient cyclic ketals or cyclic acetals may be formed at the 16,17 or 17,21 positions but are preferably acetonides or 17,21 methylene dioxy derivatives.

Suitable cyclic orthoesters that may be formed at these positions include the 17,21 methylorthoacetate, the 17,21 ethylorthopropionate, the 17,21 methylorthobenzoate and the 17,21 methylorthovalerate. One preferred class of compounds of the invention are those wherein $R_3$ represents H or $\alpha$OQ, especially OH.

Another preferred class of compounds of the invention are those wherein $R_3$ represent $\alpha$ or $\beta$ methyl, most preferably $\alpha$ methyl.

It is often preferred that Y should be halogen. X can also be halogen and thus some preferred compounds of the invention have both X and Y representing halogen, usually both representing chlorine or both representing bromine.

However, it is generally preferred that Y shall represent halogen and X shall represent OQ, preferably OH.

Preferred values of Y are bromine and, especially, fluorine. Thus particularly preferred compounds of the invention are 9α-halo (especially fluoro) 11β-hydroxy compounds.

It is of course already well known to make pregna-1,4-diene-3,20-dione compounds. It is also known to produce a few 2-chloro steroids.

Further, it is well known to make 6α-fluoro steroids. There have been some references to the production of 6β-fluoro steroids in the literature but it seems to have been considered generally in the art that 6β-fluoro steroids are inferior pharmaceutically to 6α-fluoro steroids. The combination of 2-chloro with 6β-fluoro in pregna-1,4-diene-3,20-diones appears to be new and gives good anti-inflammatory activity with low or negligible side effects as discussed above.

New compounds of the present invention to be particularly emphasized are:

9α-bromo-2-chloro-6β-fluoro-11β,17α,21-trihydroxy-pregna-1,4-diene-3,20-dione-17,21-diacetate (6a)

9α-bromo-2-chloro-6β-fluoro-11β,17α,21-trihydroxy-16α-methyl-pregna-1,4-diene-3,20-dione-17,21-diacetate (6b)

9α-bromo-2-chloro-6β-fluoro-11β,17α,21-trihydroxy-16β-methyl-pregna-1,4-diene-3,20-dione-17,21-diacetate (6c)

2-chloro-6β,9α-difluoro-11β,17α,21-trihydroxy-pregna-1,4-diene-3,20-dione-17,21-diacetate (8a)

2-chloro-6β,9α-difluoro-11β,17α,21-trihydroxy-16α-methyl-pregna-1,4-diene-3,20-dione-17,21-diacetate (8b)

2-chloro-6β,9α-difluoro-11β,17α,21-trihydroxy-16β-methyl-pregna-1,4-diene-3,20-dione-17,21-diacetate (8c)

2,9α-dichloro-6β-fluoro-11β,17α,21-trihydroxy-pregna-1,4-diene-3,20-dione-17,21-diacetate (8d)

2,9α-dichloro-6β-fluoro-11β,17α,21-trihydroxy-16α-methyl-pregna-1,4-diene-3,20-dione-17,21-diacetate (8e)

2,9α-dichloro-6β-fluoro-11β,17α,21-trihydroxy-16β-methyl-pregna-1,4-diene-3,20-dione-17,21-diacetate (8f)

2,9α,11β-trichloro-6β-fluoro-17α,21-dihydroxy-pregna-1,4-diene-3,20-dione-17,21-diacetate (8g)

2,9α,11β-trichloro-6β-fluoro-17α,21-dihydroxy-16α-methyl-pregna-1,4-diene-3,20-dione-17,21-diacetate (8h)

2,9α,11β-trichloro-6β-fluoro-17α,21-dihydroxy-16β-methyl-pregna-1,4-diene-3,20-dione-17,21-diacetate (8i)

2-chloro-6β,9α-difluoro-11β,17α,21-trihydroxy-pregna-1,4-diene-3,20-dione (8j)

2-chloro-6β,9α-difluoro-11β,17α,21-trihydroxy-16α-methyl-pregna-1,4-diene-3,20-dione (8k)

2-chloro-6β,9α-difluoro-11β,17α,21-trihydroxy-16β-methyl-pregna-1,4-diene-3,20-dione (8l)

2,9α,11β-trichloro-6β-fluoro-17α,21-dihydroxy-pregna-1,4-diene-3,20-dione (8m)

2,9α,11β-trichloro-6β-fluoro-17α,21-dihydroxy-16α-methyl-pregna-1,4-diene-3,20-dione (8n)

2,9α,11β-trichloro-6β-fluoro-17α,21-dihydroxy-16β-methyl-pregna-1,4-diene-3,20-dione (8o)

2-chloro-6β,9α-difluoro-11β,17α,21-trihydroxy-pregna-1,4-diene-3,20-dione-21-acetate (8p)

2-chloro-6β,9α-difluoro-11β,17α,21-trihydroxy-16α-methyl-pregna-1,4-diene-3,20-dione-21-acetate (8q)

2-chloro-6β,9α-difluoro-11β,17α,21-trihydroxy-16β-methyl-pregna-1,4-diene-3,20-dione-21-acetate (8r)

2,9α,11β-trichloro-6β-fluoro-17α,21-dihydroxy-pregna-1,4-diene-3,20-dione-21-acetate (8s)

2,9α,11β-trichloro-6β-fluoro-17α,21-dihydroxy-16α-methyl-pregna-1,4-diene-3,20-dione-21-acetate (8t)

2,9α,11β-trichloro-6β-fluoro-17α,21-dihydroxy-16β-methyl-pregna-1,4-diene-3,20-dione-21-acetate (8u)

2-chloro-6β,9α-difluoro-11β,17α,21-trihydroxy-pregna-1,4-diene-3,20-dione-21-hemisuccinate (8v)

2-chloro-6β,9α-difluoro-11β,17α,21-trihydroxy-16α-methyl-pregna-1,4-diene-3,20-dione-21-hemisuccinate (8w)

2-chloro-6β,9α-difluoro-11β,17α,21-trihydroxy-16β-methyl-pregna-1,4-diene-3,20-dione-21-hemisuccinate (8z)

2-chloro-6β,9α-difluoro-11β,17α,21-trihydroxy-pregna-1,4-diene-3,20-dione-21-hemisuccinate sodium salt (8aa)

2-chloro-6β,9α-difluoro-11β,17α,21-trihydroxy-16α-methyl-pregna-1,4-diene-3,20-dione-21-hemisuccinate sodium salt (8ab)

2-chloro-6β,9α-difluoro-11β,17α,21-trihydroxy-16β-methyl-pregna-1,4-diene-3,20-dione-21-hemisuccinate sodium salt (8ac)

2-chloro-6β,9α-difluoro-11β,17α,21-trihydroxy-pregna-1,4-diene-3,20-dione-17-valerate (8ad)

2-chloro-6β,9α-difluoro-11β,17α,21-trihydroxy-pregna-1,4-diene-3,20-dione-17-acetate (8ae)

2-chloro-6β,9α-difluoro-11β,17α,21-trihydroxy-16α-methyl-pregna-1,4-diene-3,20-dione-17-acetate (8af)

2-chloro-6β,9α-difluoro-11β,17α,21-trihydroxy-16β-methyl-pregna-1,4-diene-3,20-dione-17-acetate (8ag)

2,9α,11β-trichloro-6β-fluoro-17α,21-dihydroxy-pregna-1,4-diene-3,20-dione-17-acetate (8ah)

2,9α,11β-trichloro-6β-fluoro-17α,21-dihydroxy-16α-methyl-pregna-1,4-diene-3,20-dione-17-acetate (8ai)

2,9α,11β-trichloro-6α-fluoro-17α,21-dihydroxy-16β-methyl-pregna-1,4-diene-3,20-dione-17-acetate (8aj)

2-chloro-6β,9α-difluoro-11β,17α,21-trihydroxy-pregna-1,4-diene-3,20-dione-17,21-acetonide (8ak)

2-chloro-6β,9α-difluoro-11β,17α,21-trihydroxy-16α-methyl-pregna-1,4-diene-3,20-dione-17,21-acetonide (8al)

2-chloro-6β,9α-difluoro-11β,17α,21-trihydroxy-16β-methyl-pregna-1,4-diene-3,20-dione-17,21-acetonide (8am)

2-chloro-6β,9α-difluoro-11β,16α,17α,21-tetrahydroxy-pregna-1,4-diene-3,20-dione-21-acetate (10a)

2-chloro-6β,9α-difluoro-11β,16α,17α,21-tetrahydroxy-pregna-1,4-diene-3,20-dione (10b)

2-chloro-6β,9α-difluoro-11β,16α,17α,21-tetrahydroxy-pregna-1,4-diene-3,20-dione-16,17-acetonide-21-acetate (11a)

2-chloro-6β,9α-difluoro-11β,16α,17α,21-tetrahydroxy-pregna-1,4-diene-3,20-dione-16,17-acetonide (11b)

2-chloro-6β,9α-difluoro-11β,16α,17α,21-tetrahydroxy-pregna-1,4-diene-3,20-dione-16,21-diacetate (12a)

The novel compounds of the invention have good anti-inflammatory activity. This activity can be exhibited upon conventional methods of administration, for example topically and systemically.

Some compounds give best results topically while others give best results systemically, for instance when taken orally as is preferred. Because of the very high activity possessed by preferred compounds of the invention lower dosages can be used than are useful with known anti-inflammatory steroids; even at conventional dosages preferred compounds of the invention have much less, and generally no, side effects compared with known anti-inflammatory steroids.

The compounds of the invention are useful for treatment of a wide variety of inflammatory conditions, for example in the treatment of inflammatory conditions of the skin, eyes and ears of humans and of valuable domestic animals, as well as contact dermatitis and other allergic reactions and also possess valuable antirheumatoid arthritic properties.

Therapeutic compositions of the invention comprise a compound of the invention together with a pharmaceutically acceptable liquid or solid carrier. Any therapeutically acceptable and effective concentration of the compound in the composition may be used. Any suitable composition may be prepared, according to the chosen manner of administration. Suitable compositions include pills, tablets, capsules, solutions syrups or elixirs for oral use, liquid forms of the types used to make injectable compositions of the natural and synthetic cortical steroids hormones, and topical compositions, for example in the form of ointments, creams and lotions.

The compositions may also include coacting antibiotics, germicides or other materials forming advantageous combination therewith.

weight increase even at very high concentrations (40 micrograms/pellet).

The most active compounds inhibit the cotton-pellet induced granuloma at doses ranging from 0.01 to 1 microgram/pellet whereas hydrocortisone acetate shows the same activity at about 100–200 micrograms/pellet. The systemic anti-inflammatory activity has been evaluated in rats by cotton-pellet induced granuloma test, giving the compounds orally for 8 days. The most active compounds show activity at doses ranging from 0.5 to 5 mg/kg b.w., while Hydrocortisone acetate and Methylprednisolone are active at doses ranging from 10 to 50 mg/kg b.w. Most of the compounds of the present invention have, on this test, no inhibiting action on adrenals weight and a thymolitic or body weight reducing activity lower than that displayed by the most active already known steroids.

A preferred reaction scheme for making compounds of formula A is shown below. Preferred methods of carrying out each of the process steps shown in the scheme are described subsequently.

Of course alterations to the described reaction conditions can be used: e.g. oxidising agents other than potassium permanganate and solvents other than pyridine can be used.

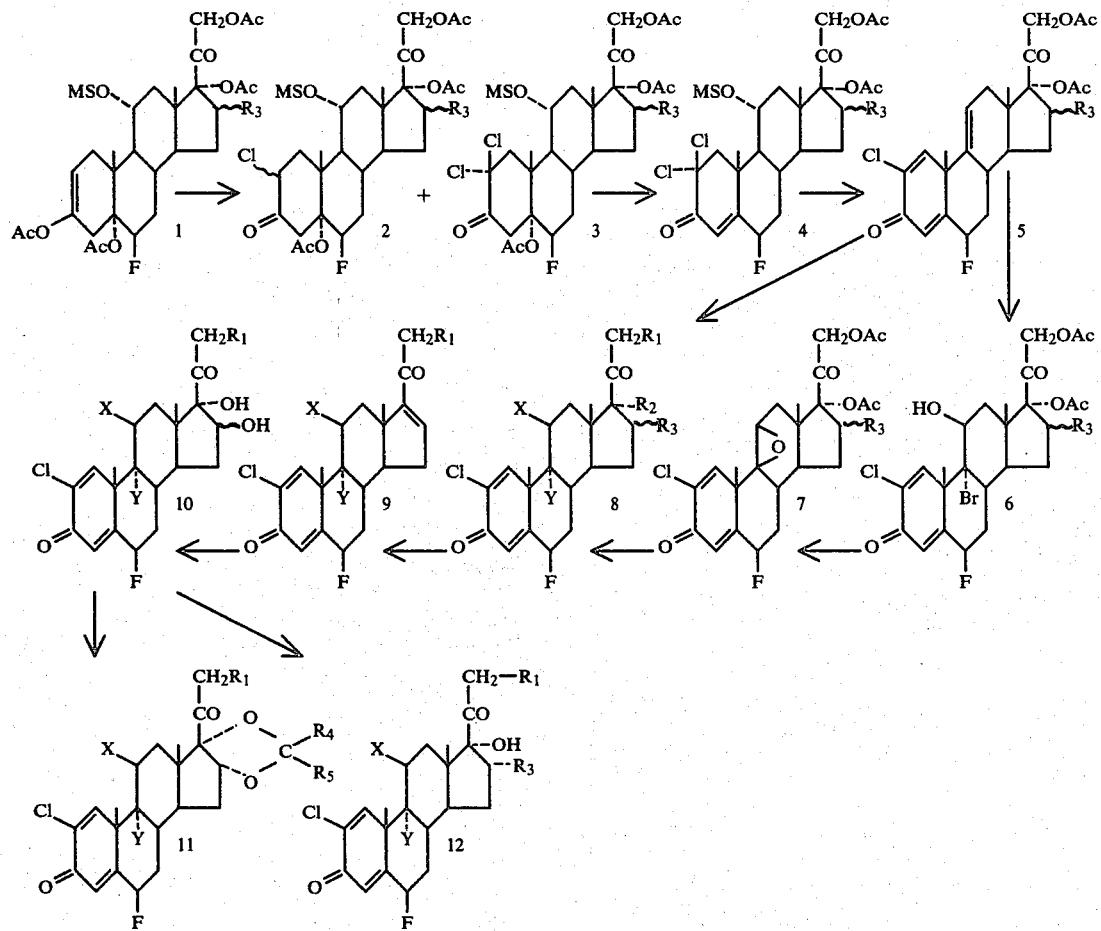

The local anti-inflammatory activity has been evaluated in rats by the cotton-pellet induced granuloma test, applying the compound directly to the pellet.

All the new compounds of the present invention show a remarkable anti-inflammatory activity without undesirable side effects on the thymus and on the body The starting substance used for the preparation of the compounds of the present invention is 6β-fluoro-3,5α,1-1α,17α,21-pentahydroxy-pregn-2-ene-20-one-3,5,17,21-tetracetate-11-mesylate or 6β-fluoro-3,5α,11α,17α,21- pentahydroxy-16-methyl-pregn-2-ene-20-one-3,5,17,21-tetracetate-11-mesylate, which are described in British Patent Application No. 55799/74. In the specification the term "16 methyl" is to be understood as meaning both 16α-methyl and 16β-methyl. Chlorination of the compound 1 with 2,5 equivalents of chlorine in dioxane produces a 80:20 mixture of chloro-compounds 2 and 3. No further chlorination is observed by repeating this experiment with a five-fold excess of chlorine.

In contrast chlorination of the mixture to give 4 is completed with only 1,2 equivalents of chlorine in acetic acid.

The combination of certain metal halides, particularly lithium chloride and bromide in hot dimethylformamide is particularly effective to obtain the corresponding triene 5 from 4.

Other amide solvents, such as dimethylacetamide and N-formylpiperidine can be used in place of dimethylformamide. A modification involves the use of an excess of lithium carbonate in dimethylformamide.

The reaction of the compound 5 with hypobromous acid produces the corresponding 9α-bromo compound 6. When this 9α-bromo compound is reacted with potassium carbonate the 9β,11β-oxido compound 7 is obtained. Reaction of the latter compound with hydrofluoric acid affords 8 where X=OH and Y=F, which upon hydrolysis is converted into the corresponding free alcohol.

Reaction of 7 with hydrochloric acid affords 8 where X=OH and Y=Cl. The triene 5 is reacted with N-chlorosuccinimide in presence of lithium chloride to obtain 8 where X=Y=Cl, which by hydrolysis is converted into the corresponding free alcohol.

The fluorine atom at the 6β-position of the compound 8 is considered to be in the stable configuration on the basis of the following observation. Attempts to isomerize it with dry hydrochloric acid in chloroform at 0° C. for 2 hrs. do not alter the optical rotatory dispersing curve of the crude product.

Recrystallization affords pure product identical in all aspects to the starting sample.

When the compound 8a (X OH, Y=F, $R_3$=H, $R_1$=$R_2$—OCOCH$_3$) is reacted with potassium acetate in hot dimethylformamide the 2-chloro-6β,9α-difluoro-11β,21-dihydroxy-pregna-1,4,16-triene-21-acetate (9α X=OH, Y=F $R_1$=OCOCH$_3$) is obtained and this is then oxidated with potassium permanganate to produce the corresponding 2-chloro-6β,9α-difluoro-11β,16α,1-7α,21-tetrahydroxy-pregna-1,4-diene-3,20-dione-21-acetate (10α X=OH, Y=F $R_1$=OCOCH$_3$) which upon hydrolysis is converted into the corresponding free alcohol.

Esterification of the hydroxyl function at the 21-position is conveniently effected with a lower fatty acid anhydride, such as acetic anhydride, or preferably with a lower aliphatic acid chloride such as acetic acid chloride in presence of pyridine, which simultaneously serves as solvent.

The 17α-esters are prepared by treatment of the corresponding 17α,21 diols with a lower alkyl orthoesters in presence of an acid catalyst followed by acid hydrolysis of the resulting 17α,21-orthoester (a mixture of two epimeric orthoesters).

The esterification of the hydroxyl function at the 11-position is effected with a lower fatty acid anhydride in presence of perchloric acid or p-toluensulfonic acid.

The esterification of the hydroxyl function at the 21-position can also be achieved by trans-esterification of the corresponding 17α-esters.

Treatment of the corresponding 17α,21-diols with 2,2-dimethoxy-propane in presence of p-toluensulfonic acid produces the 17,21-acetonides.

Treatment of the compounds 10 with acetone and perchloric acid produces the 16,17-acetonides.

The esterification of the hydroxyl function at the 16-position of the compounds 10 is effected with a lower fatty acid anhydride in presence of pyridine which simultaneously serves as solvent.

EXAMPLE I

A solution of 15.75 g. of 6β-fluoro-3,5α,11α,17α,21-pentahydroxy-pregn-2-ene-20-one-3,5,17,21-tetracetate-11-mesylate (1a, $R_3$=H) in 180 ml. of dioxane containing 0.54 g. of chlorine, was stirred at 5°–10° C. for 1 hr. and then poured into 1000 ml. of water and 45 g. of sodium chloride. The product was collected by filtration, washed neutral with water and dried (16 g.).

NMR of this material indicated a ~80:20 mixture of 2-chloro-6β-fluoro-5α,11α,17α,21-tetrahydroxy-pregnan-3,20-dione-5,17,21-triacetate-11-mesylate (2a, $R_3$=H) and 2,2-dichloro-6β-fluoro-5α,11α,17α,21-tetrahydroxy-pregnan-3,20-dione-5,17,21,triacetate-11-mesylate (3a, $R_3$=H).

The filtered solid was utilized in the next reaction without further purification.

EXAMPLE II

Using the general procedure of Example I the 6β-fluoro-3,5α,11α,17α,21-pentahydroxy-16α-methyl-pregn-2-ene-20-one-3,5,17,21-tetracetate-11-mesylate (1b, $R_3$=αCH$_3$) was converted into the mixture of 2-chloro-6β-fluoro-5α,11α,17α,21-tetrahydroxy-16α-methyl-pregnan-3,20-dione-5,17,21-triacetate-11-mesylate (2b, $R_3$=αCH$_3$) and 2,2-dichloro-6β-fluoro-5α,1-1α,17α,21-tetrahydroxy-16α-methyl-pregnan-3,20-dione-5,17,21-triacetate-11-mesylate (3b, $R_3$=αCH$_3$). The mixture was utilized in the next reaction without further purification.

EXAMPLE III

Using the general procedure of Example I the 6β-fluoro-3,5α,11α,17α,21-pentahydroxy-16β-methyl-pregn-2-ene-20-one-3,5,17,21-tetracetate-11-mesylate (1c, $R_3$=βCH$_3$) was converted into the mixture of 2-chloro-6β-fluoro-5α,11α,17α,21-tetrahydroxy-16β-methyl-pregnan-3,20-dione-5,17,21-triacetate-11-mesylate (2c, $R_3$=βCH$_3$) and 2,2-dichloro-6β-fluoro-5α,1-1α,17α,21-tetrahydroxy-16β-methyl-pregnan-3,20-dione-5,17,21-triacetate-11-mesylate (3c, $R_3$=βCH$_3$).

The mixture was utilized in the next reaction without further purification.

EXAMPLE IV 16 g. of the mixture of 2-chloro-6β-fluoro-5α,11α,1-7α,21-tetrahydroxy-pregnan-3,20-dione-5,17,21-triacetate-11-mesylate (2a, $R_3$=H) and 2,2-dichloro-6β-fluoro-5α,11α,17α,21-tetrahydroxy-pregnan-3,20-dione-5,17,21-triacetate-11-mesylate (3a, $R_3$=H), obtained in Example I, were dissolved in 500 ml. of anhydrous acetic acid at 90° C. A solution of sodium acetate (38.5 g. dried at 100° C.) in acetic acid (500 ml.) at 90° C. was added, followed immediately by 30 ml. of 1 M chlorine solution in acetic acid, added in one portion. The solution was stirred at 90° C. for 20 min., cooled at 20° C., stirred for 0.5 hr., poured into a mixture of 700 ml. of ice and water.

The resulting pricipitate was collected by filtration and dissolved in chloroform. The solution was washed with water, 5% NaHCO$_3$ and water, dried and concentrated.

The residue was crystallized from ethanol to give 7 g. of 2,2-dichloro-6β-fluoro-11α,17α,21-trihydroxy-pregn-4-ene-3,20-dione-17,21-diacetate-11-mesylate (4a, R$_3$=H) characterized by M.P. 173°-5° C. (decomposition).
$[\alpha]_D^{20}$ −12° (C 1.0 in chloroform).
λ max (methanol) 243 mμ (ε11200).
IR(KBr) 1745, 1730, 1710, 1625, 1240 cm$^{-1}$.
NMR (CDCl$_3$-TMS) Hz at 60 mHz 364,360 (d, 1, C$_4$-H) 328,278 (doublet of triplets, 1, C$_6$-H) 320–290 (m, 1, C$_{11}$-H) 302,286,280,264 (doublet of doublets, 2, —COCH$_2$O—) 190 (S, 3, —OSO$_2$CH$_3$) 130 (S, 1, OAc) 128 (S, 1, OAc) 106,102 (d, 3, C$_{10}$-CH$_3$ split by 6βF) 52 (S, 1, C$_{13}$-CH$_3$).

Analysis: Calcd. for C$_{26}$H$_{33}$Cl$_2$FO$_9$S (percent): C 51.07; H 5.44; Cl 11.59; F 3.11; S 5.24. Found (percent): C 50.89; H 5.44; Cl 11.67; F 3.09; S 5.27.

EXAMPLE V

Using the general procedure of Example IV the mixture of 2-chloro-6β-fluoro-5α,11α,17α,21-tetrahydroxy-16α-methyl-pregnan-3,20-dione-5,17,21-triacetate-11-mesylate (2b, R$_3$=αCH$_3$) and 2,2-dichloro-6β-fluoro-5α,11α,17α,21-tetrahydroxy-16α-methyl-pregnan-3,20-dione-5,17,21-triacetate-11-mesylate (3b, R$_3$=αCH$_3$), obtained in Example II, was converted into 2,2-dichloro-6β-fluoro-11α,17α,21-trihydroxy-16α-methyl-pregn-4-ene-3,20-dione-17,21-diacetate-11-mesylate (4b, R$_3$ααCH$_3$)

IR(KBr) 1750, 1730, 1708, 1630, 1235 cm$^{-1}$.
Analysis: Calcd. for C$_{27}$H$_{35}$Cl$_2$FO$_9$S (percent): C 51.84; H 5.64; Cl 11.34; F 3.04; S 5.13. Found (percent): C 52.04; H 5.70; Cl 11.32; F, 3.07; S 5.12.

EXAMPLE VI

Using the general procedure of Example IV the mixture of 2-chloro-6β-fluoro-5α,11α,17α,21-tetrahydroxy-16β-methyl-pregnan-3,20-dione-5,17,21-triacetate-11-mesylate (2c, R$_3$=ηCH$_3$) and 2,2-dichloro-6β-fluoro-5α,11α,17α,21-tetrahydroxy-16β-methyl-pregnan-3,20-dione-5,17,21-triacetate-11-mesylate (3c, R$_3$=βCH$_3$), obtained in Example III, was converted into 2,2-dichloro-6β-fluoro-11α,17α,21-trihydroxy-16β-methyl-pregn-4-ene-3,20-dione-17,21-diacetate-11-mesylate (4c, R$_3$=αCH$_3$).

IR(KBr) 1745, 1730, 1710, 1630, 1235 cm$^{-1}$.
Analysis: Calcd. for C$_{27}$H$_{35}$Cl$_2$FO$_9$S (percent): C 51,84; H 5,64; Cl 11,34; F 3.04; S 5.13. Found (percent): C 51.90; H 5.62; Cl 11.29; F 3.04; S 5.18.

EXAMPLE VII 14.8 g. of 2,2-dichloro-6β-fluoro-11α,17α,21-trihydroxy-pregn-4-ene-3,20-dione-17,21-diacetate-11-mesylate (4a, R$_3$=H) were added, in one portion, to a mixture of 120 ml. of dimethylformamide, 30 g. of lithium carbonate and 15 g. of lithium bromide under stirring at 100° C. The reaction mixture was then refluxed at 130° C. under nitrogen for 0.5 hr., cooled and poured into cold water. The precipitate was filtered off, washed with water, dried and absorbed on FLORISIL (Registered Trade Mark) (ratio 1:100) from 8:2 chloroform-benzene. Elution with chloroform gave fractions which were recrystallized from benzene to give 4 g. of 2-chloro-6β-fluoro-17α,21-dihydroxy-pregna-1,4,9(11)-triene-3,20-dione-17,21-diacetate (5a,R$_3$=H) characterized by M.P. 264'-6° C. (decomposition).
$[\alpha]_D^{20}$ −73° (C 1.0 m chloroform).
IR(KBr) 1740, 1680, 1650, 1610, 1235 cm$^{-1}$.
NMR (CDCl$_3$-TMS) Hz at 60 mHz 435 (S, 1, C$_1$—H) 374,370 (d, 1, C$_4$—H) 344–334 (m, 1, C$_{11}$—H) 330, 280 (doublet of triplets, 1, C$_6$—H) 300, 284, 278, 262 (doublet of doublets, 2, —COCH$_2$O—) 128 (S, 1, OAc) 122 (S, 1, OAc) 94,92 (d, 3, C$_{10}$—CH$_3$ split by 6βF) 45 (S, 1, C$_{13}$—CH$_3$).

Analysis: Calcd. for C$_{25}$H$_{28}$ClFO$_6$ (percent): C 62.70; H 5.89; Cl 7.40; F 3.97. Found (percent): C 62.75; H 5.92; Cl 7.35; F 3.95.

EXAMPLE VIII

Using the general procedure of Example VII the 2,2-dichloro-6β-fluoro-11α,17α,21-trihydroxy-16α-methyl-pregn-4-ene-3,20-dione-17,21-diacetate (4b, R$_3$=αCH$_3$) was converted into 2-chloro-6β-fluoro-17α,21-dihydroxy-16α-methyl-pregna-1,4,9(11)-triene-3,20-dione-17,21-diacetate (5b, R$_3$=αCH$_3$) characterized by IR(KBr) 1740, 1680, 1645, 1235 cm$^{-1}$.
Analysis: Calcd. for C$_{26}$H$_{30}$ClFO$_6$ (percent): C 63.35; H 6.13; Cl 7.19; F 3.85. Found (percent): C 63.45; H 6.15; Cl 7.21; F 3.86.

EXAMPLE IX

Using the general procedure of Example VII the 2,2-dichloro-6β-fluoro-11α,17α,21-trihydroxy-16β-methyl-pregn-4-ene-3,20-dione-17,21-diacetate (4c, R$_3$=βCH$_3$) was converted into 2-chloro-6β-fluoro-17α,21-dihydroxy-16β-methyl-pregna-1,4,9(11)-triene-3,20-dione-17,21-diacetate (5c, R$_3$=βCH$_3$) characterized by IR(KBr) 1745, 1675, 1650, 1230 cm$^{-1}$.
Analysis: Calcd. for C$_{26}$H$_{30}$ClFO$_6$ (percent): C 63.35; H 6.13; Cl$^-$7.19; F 3.85. Found (percent): C 63.25; H 6.12; Cl 7.24; F 3.89.

EXAMPLE X 2.8 g. of 1,3-dibromo-5,5-dimethyl-hydantoin were added in the dark at 15° C. under stirring over a period of 0.5 hr. to a suspension of 3.63 g. of 2-chloro-6β-fluoro-17α,21-dihydroxy-pregna-1,4,9(11)-triene-3,20-dione-17,21-diacetate (5a, R$_3$=H) in 90 ml. of tetrahydrofurane and 0.45 g. of 70% perchloric acid in 4.5 ml. of water. During the addition the suspension began to thin and after a total reaction time of 45 min. all the starting material was dissolved. After an additional 2 hr., 10% sodium sulfite aqueous solution was added under stirring until KJ-starch paper was no longer blued. The solution was slowly poured into 250 ml. cold water, the solid was filtered and utilized moist in the next reaction.

The 9α-bromo-2-chloro-6β-fluoro-11β,17α,21-trihydroxy-pregna-1,4-diene-3,20-dione-17,21-diacetate (6a, R$_3$=H) was filtered and utilized moist in the next reaction. Analytically pure 6a was obtained by crystallization from acetone-hexane.

M.P. 212°-4° C. (decomposition).
$[\alpha]_D^{20}$ −11° (C 1.0 in chloroform).
IR(KBr) 3420 (broad), 3325, 1755, 1740, 1675, 1645, 1610, 1235 cm$^{-1}$.

Analysis: Calcd. for $C_{25}H_{29}BrClFO_7$ (percent): C 52.14; H 5.08; Br 13.88; Cl 6.16; F 3.30. Found (percent): C 52.37; H 5.08; Br 13.81; F 3.25.

EXAMPLE XI

Using the general procedure of Example X the 2-chloro-6β-fluoro-17α,21-dihydroxy-16α-methyl-pregna-1,4,9(11)-triene-3,20-dione-17,21-diacetate (5b, $R_3=\alpha CH_3$) was converted into 9α-bromo-2-chloro-6β-fluoro-11β,17α,21-trihydroxy-16α-methyl-pregna-1,4-diene-3,20-dione-17,21-diacetate (6b, $R_3=\alpha CH_3$) characterized by IR(KBr) 3430 (broad), 1750, 1740, 1680, 1640, 1605, 1230 cm$^{-1}$.

Analysis: Calcd. for $C_{26}H_{31}BrClFO_7$ (percent): C 52.94; H 5.30; Br 13.55; Cl 6.01; F 3.22. Found (percent): C 52.92; H 5.35; Br 13.51; Cl 6.10; F 3.25.

However the product 6b was filtered and utilized moist in the next reaction.

EXAMPLE XII

Using the general procedure of Example X the 2-chloro-6β-fluoro-17α,21-dihydroxy-16β-methyl-pregna-1,4,9(11)-triene-3,20-dione-17,21-diacetate (5c, $R_3=\beta CH_3$) was converted into 9α-bromo-2-chloro-6β-fluoro-11β,17α,21-trihydroxy-16β-methyl-pregna-1,4-diene-3,20-dione-17,21-diacetate (6c, $R_3=\beta CH_3$) characterized by IR(KBr) 3425 (broad), 1755, 1740, 1675, 1645, 1605, 1230 cm$^{-1}$.

Analysis: Calcd. for $C_{26}H_{31}BrClFO_7$ (percent): C 52.94; H 5.30; Br 13.55; Cl 6.01; F 3.22. Found (percent): C 53.07; H 5.33; Br 13.30; Cl 6.05; F 3.20.

However the product 6c was filtered and utilized moist in the next reaction.

EXAMPLE XIII 12 ml. of a 14% potassium carbonate aqueous solution were added over a period of 20 min. at 20° C. under stirring to the solution of the moist product (6a, $R_3=H$) 9α-bromo-2-chloro-6β-fluoro-11β,17α,21-trihydroxy-pregna-1,4-diene-3,20-dione-17,21-diacetate [obtained in Example X from 2.8 g. of the product 5a ($R_3=H$)] in 75 ml. of acetone. The solution was stirred for 3.5 hr. Ice water was added under stirring, upon which crystallization occurs rapidly. The product 2-chloro-6β-fluoro-17α,21-dihydroxy-9β,11β-oxido-pregna-1,4-diene-3,20-dione-17,21-diacetate (7a, $R_3=H$) was filtered, washed with water, dried and characterized by M.P. 255°–6° C. (decomposition).

$[\alpha]_D^{20} -78°$ (C 1.0 in chloroform).

IR(KBr) 1760, 1745, 1735, 1670, 1645, 1605, 1235 cm$^{-1}$.

Analysis: Calcd. for $C_{25}H_{28}ClFO_7$ (percent): C 60.67; H 5.70; Cl 7.16; F 3.84. Found (percent): C 60.35; H 5.72; Cl 7.23; F 3.80.

EXAMPLE XIV

Using the general procedure of Example XIII the 9α-bromo-2-chloro-6β-fluoro-11β,17α,21-trihydroxy-16α-methyl-pregna-1,4-diene-3,20-dione-17,21-diacetate (6b, $R_3=\alpha CH_3$) was converted into 2-chloro-6β-fluoro-17α,21-dihydroxy-16α-methyl-9β,11β-oxido-pregna-1,4-diene-3,20-dione-17,21-diacetate (7b, $R_3=\alpha CH_3$) characterized by IR(KBr) 1750, 1740, 1670, 1640, 1605, 1230 cm$^{-1}$.

Analysis: Calcd. for $C_{26}H_{30}ClFO_7$ (percent): C 61.36; H 5.94; Cl 6.97; F 3.73. Found (percent): C 61.12; H 5.87; Cl 7.02; F 3.75.

EXAMPLE XV

Using the general procedure of Example XIII the 9α-bromo-2-chloro-6β-fluoro-11β,17α,21-trihydroxy-16β-methyl-pregna-1,4-diene-3,20-dione-17,21-diacetate (6c, $R_3=\beta CH_3$) was converted into 2-chloro-6β-fluoro-17α,21-dihydroxy-16β-methyl-9β,11β-oxido-pregna-1,4-diene-3,20-dione-17,21-diacetate (7c, $R_3=\beta CH_3$) characterized by IR(KBr) 1755, 1740, 1675, 1645, 1605, 1230 cm$^{-1}$.

Analysis: Calcd. for $C_{26}H_{30}ClFO_7$ (percent): C 61.36; H 5.94; Cl 6.97; F 3.73. Found (percent): C 61.46; H 6.01; Cl 6.92; F 3.80.

EXAMPLE XVI 40 ml of a 70% hydrofluoric acid aqueous solution were cooled to $-10°$ C. in a polyethylene flask equipped with electromagnetic stirrer, 3.3 g. of 2-chloro-6β-fluoro-17α,21-dihydroxy-9β,11β-oxido-pregna-1,4-diene-3,20-dione-17,21-diacetate (7a, $R_3=H$) were added under stirring during 15 min. After 1.5 hr. the reaction mixture was precipitated in water and ammonia. The solid was collected by filtration, washed with water and dried to a constant weight, giving about 3 g. of 2-chloro-6β,9α-difluoro-11β,17α,21-trihydroxy-pregna-1,4-diene-3,20-dione-17,21-diacetate (8a, X=OH, Y=F, $R_1=R_2=OCOCH_3$, $R_3=H$).

Crystallization from benzene gave 2.5 g. of pure product.

M.P. 285°–6° C. (decomposition).

$[\alpha]_D -24°$ (C 0.5 in chloroform).

λmax (methanol) 244–5 mμ (ε13700).

IR(KBr) 3520, 1755, 1730, 1705, 1680, 1645, 1610, 1230 cm$^{-1}$.

NMR (dimethyl-$d_6$ sulfoxide-TMS) Hz at 60 mHz 452 (S, 1, $C_1$-H) 390,386 (d, 1, $C_4$-H) 346,296 (doublet of triplets, 1, $C_6$-H) 337,332 (d, 1, $C_{11}$-OH) 286 (S, 2, —$CH_2OAc$) 264–240 (m, 1, $C_{11}$-H) 126 (S, 3, OAc) 120 (S, 3, OAc) 98,94 (d, 3, $C_{10}$-$CH_3$ split by 6βF) 55 (S, 3, $C_{13}$-$CH_3$).

Analysis: Calcd. for $C_{25}H_{29}ClF_2O_7$ (percent): C 58.31; H 5.68; Cl 6.88; F 7.38. Found (percent): C 58.50; H 5.72; Cl, 6.83; F 7.43.

EXAMPLE XVII

Using the general procedure of Example XVI the 2-chloro-6β-fluoro-17α,21-dihydroxy-16α-methyl-9β,11β-pregna-1,4-diene-3,20-dione-17,21-diacetate (7b, $R_3=\alpha CH_3$) was converted into 2-chloro-6β,9α-difluoro-11β,17α,21-trihydroxy-16α-methyl-pregna-1,4-diene-3,20-dione-17,21-diacetate (8b, X=OH, Y=F, $R_1=R_2=OCOCH_3$, $R_3=\alpha CH_3$) characterized by IR(KBr) 3525, 1755, 1730, 1705, 1680, 1640, 1610, 1230 cm$^{-1}$.

Analysis: Calcd. for $C_{26}H_{31}ClF_2O_7$ (percent): C 59.04; H 5.91; Cl 6,70; F 7.18. Found (percent): C 59.11; H 5.92; Cl 6.75; F 7.12.

EXAMPLE XVIII

Using the general procedure of Example XVI the 2-chloro-6β-fluoro-17α,21-dihydroxy-16β-methyl-9β,11β-oxido-pregna-1,4-diene-3,20-dione-17,21-diacetate (7c, $R_3=\beta CH_3$) was converted into 2-chloro- 6β,9α-difluoro-11β;17α,21-trihydroxy-16β-methyl-pregna-1,4-diene-3,20-dione-17,21-diacetate (8c, X=OH, Y=F, R₁=R₂=OCOCH₃, R₃=CH₃) characterized by IR(KBr) 3520, 1755, 1740, 1710, 1680, 1640, 1610, 1235 cm⁻¹.

Analysis: Calcd. for $C_{26}H_{31}ClF_2O_7$ (percent): C 59.04; H 5.91; Cl 6.70; F 7.18. Found (percent): C 58.93; H 5.80; Cl 6.65; F 7.14.

EXAMPLE XIX 50 ml. of hydrochloric acid were added at 0° C. over a period of 40 min. to a suspension of 5 g. of 2-chloro-6β-fluoro-17α,21-dihydroxy-9β,11β-oxide-pregna-1,4-diene-3,20-dione-17,21-diacetate (7a, R₃=H) in 30 ml. of acetone. The mixture was held at 0° C. with stirring for about 15 min. and then the precipitated 2,9α-dichloro-6β-fluoro-11β,17α,21-trihydroxy-pregna-1,4-diene-3,20-dione-17,21-diacetate (8d, X=OH, Y=Cl, R₃=H, R₁=R₂=OCOCH₃) was recovered by filtration, washed repeatedly with water and dried (4.9 g.).

IR(KBr) 3440 (broad), 1755, 1740, 1705, 1675, 1640, 1600, 1230 cm⁻¹.

Analysis: Calcd. for $C_{25}H_{29}Cl_9FO_7$ (percent): C 56.51; H 5.50; Cl 13.34; F 3.57. Found (percent): C 56.55; H 4.57; Cl 13.28; F 3.53.

EXAMPLE XX

Using the general procedure of Example XIX the 2-chloro-6β-fluoro-17α,21-dihydroxy-16α-methyl-9β,11β-oxido-pregna-1,4-diene-3,20-dione-17,21-diacetate (7b, R₃=αCH₃) was converted into 2,9α-dichloro-6β-fluoro-11β, 17α,21-trihydroxy-16α-methyl-pregna-1,4-diene-3,20-dione-17,21-diacetate (8e, X=OH, Y=Cl, R₃=αCH₃, R₁=R₂=OCOCH₃)

IR(KBr) 3445 (broad), 1755, 1740, 1705, 1675, 1640, 1600, 1230 cm⁻¹.

Analysis: Calcd. for $C_{26}H_{31}Cl_2FO_7$ (percent): C 57.25; H 5.73; Cl 13.00; F 3.48. Found (percent): C 57.34; H 5.71; Cl 12.95; F 3.51.

EXAMPLE XXI

Using the general procedure of Example XIX the 2-chloro-6β-fluoro-17α,21-dihydroxy-16β-methyl-9β,11β-oxido-pregna-1,4-diene-3,20-dione-17,21-diacetate (7c, R₃=βCH₃) was converted into 2,9α-dichloro-6β-fluoro-11β,17α,21-trihydroxy-16β-methyl-pregna-1,4-diene-3,20-dione-17,21-diacetate (8f, X=OH, Y=Cl, R₁=R₂=OCOCH₃, R₃=βCH₃) characterized by IR(KBr) 3440 (broad), 1750, 1738, 1705, 1675, 1645, 1605, 1230 cm⁻¹.

Analysis: Calcd. for $C_{26}H_{31}Cl_2FO_7$ (percent): C 57.25; H 5.73; Cl 13.00; F 3.48; Found (percent): C 57.45; H 5.75; Cl 13.12; F 3.53.

EXAMPLE XXII

To a solution of 6.8 g. of 2-chloro-6β-fluoro-17α,21-dihydroxy-pregna-1,4,9(11)-triene-3,20-dione-17,21-diacetate (5a, R₃=H) and 2.8 g. of lithium chloride in 120 ml. of glacial acetic acid were added at 20° C. under stirring 3.4 g. of N-chlorosuccinimide. The mixture was kept at 20° C. and stirred while dropwise adding 7 ml. of a 12% hydrochloric acid tetrahydrofurane solution over a period of about 10 min. After 3.5 hr. the reaction mixture was poured into cold water, the solid was collected by filtration, washed with water and dried, giving 6 g. of 2,9α,11β-trichloro-6β-fluoro-17α,21-dihydroxy-pregna-1,4-diene-3,20-dione-17,21-diacetate (8g, X=Y=Cl, R₁=R₂=OCOCH₃, R₃=H) crystallized by methanol.

M.P. 248°–9° C. (decomposition).

$[\alpha]_D^{20}$ −3° (C 14.0 in chloroform).

λmax (methanol) 243 mμ (ε13000).

IR(KBr) 1755, 1745, 1680, 1650, 1612, 1235 cm⁻¹.

Analysis: Calcd. for $C_{25}H_{28}Cl_3FO_6$ (percent): C 54.61; H 5.13; Cl 19.34; F 3.46. Found (percent): C 54.75; H 5.09; Cl 19.25; F 3.42.

EXAMPLE XXIII

Using the general procedure of Example XXII the 2-chloro-6β-fluoro-17α,21-dihydroxy-16α-methyl-pregna-1,4,9(11)-triene-3,20-dione-17,21-diacetate (5b, R₃=αCH₃) was converted into 2,9α,11β-trichloro-6β-fluoro-17α,21-dihydroxy-16α-methyl-pregna-1,4-diene-3,20-dione-17,21-diacetate (8h, R₃=αCH₃, R₁=R₂=OCOCH₃, X=Y=Cl) characterized by IR(KBr) 1760, 1740, 1678, 1645, 1610, 1230 cm⁻¹.

Analysis: Calcd. for $C_{26}H_{30}Cl_3FO_6$ (percent): C 55.38; H 5.36; Cl 18.86; F 3.37. Found (percent): C 55.32; H 5.34; Cl 18.80; F 3.35.

EXAMPLE XXIV

Using the general procedure of Example XXII the 2-chloro-6β-fluoro-17α,21-dihydroxy-16β-methyl-pregna-1,4,9(11)-triene-3,20-dione-17,21-diacetate (5c, R₃=βCH₃) was converted into 2,9α,11β-trichloro-6β-fluoro-17α,21-dihydroxy-16β-methyl-pregna-1,4-diene-3,20-dione-17,21-diacetate (8i, R₃=βCH₃, R₁=R₂=OCOCH₃, X=Y=Cl) characterized by IR(KBr) 1755, 1740, 1680, 1640, 1605, 1230 cm⁻¹.

Analysis: Calcd. for $C_{26}H_{30}Cl_3FO_6$ (percent): C 55.38; H 5.36, Cl 18.86; F 3,37. Found (percent): C 55.59; H 5.33; Cl 18.82; F 3.35.

EXAMPLE XXV

A suspension of 2 g. of 2-chloro-6β,9α-difluoro-11,17α,21-trihydroxy-pregna-1,4-diene-3,20-dione-17,21-diacetate (8a, X=OH, Y=F, R₃=H, R₁=R₂=OCOCH₃) in 40 ml. of 1% potassium hydroxide methanolic solution was stirred under nitrogen at 0° C. for 3 hrs.

Addition of cold water, elimination of methanol in vacuo, acidification with acetic acid, filtration and crystallization from dichloroethane-petroleum ether gave 1 g. of 2-chloro-6β,9α-difluoro-11β,17α,21-trihydroxy-pregna-1,4-diene-3,20-dione (8j, X=OH, Y=F, R₁=R₂=OH, R₃=H).

M.P. 219°–21° C. (decomposition).

$[\alpha]_D^{20}$ +5° (C 1.0 in chloroform).

λmax (methanol) 245 mμ (ε11800).

IR(KBr) 3440, 1715, 1670, 1640, 1600 cm⁻¹.

Analysis: Calcd. for $C_{21}H_{25}ClF_2O_5$ (percent) C 58.54; H 5.85; Cl 8.23; F 8.82. Found (percent) C 58.75; H 5.91; Cl 8.25; F 8.91.

EXAMPLE XXVI

Using the general procedure of Example XXV the 2-chloro-6α,9α-difluoro-11β,17α,21-trihydroxy-16α-methyl-pregna-1,4-diene-3,20-dione-17,21-diacetate (8b, X=OH, Y=F, R₁=R₂=OCOCH₃, R₃=αCH₃) was converted into 2-chloro-6β,9α-difluoro-11β,17α,21-trihydroxy-16α-methyl-pregna-1,4-diene-3,20-dione (8k, X=OH, Y=F, R₁=R₂=OH, R₃=αCH₃).

IR(KBr) 3440, 1712, 1670, 1640, 1600 cm⁻¹.

Analysis Calcd. for $C_{22}H_{27}ClF_2O_5$ (percent): C 59.39; H 6.12; Cl 7.97; F 8.54; Found (percent): C 59.46 H 6.21; Cl 8.06; F 8.61.

EXAMPLE XXVII

Using the general procedure of Example XXV the 2-chloro-6β,9α-difluoro-11β,17α,21-trihydroxy-16β-methyl-pregna-1,4-diene-3,20-dione-17,21-diacetate (8c, X=OH, Y=F, $R_1=R_2$=OCOCH$_3$, $R_3$=βCH$_3$) was converted into 2-chloro-6β,9α-difluoro-11β, 17α,21-trihydroxy-16β-methyl-pregna-1,4-diene-3,20-dione (8lb, X=OH, Y=F, $R_1=R_2$OH, $R_3$=βCH$_3$).

IR (KBr) 3430, 1715, 1675, 1645, 1605 cm$^{-1}$.

Analysis: Calcd. for $C_{22}H_{27}ClF_2O_5$ (percent) C 59.39; H 6.12; Cl 7.97; F 8.54. Found (percent) C 59.43; H 6.12; Cl 7.98; F 8.60.

EXAMPLE XXVIII

Using the general procedure of Example XXV the 2,9α,11β-trichloro-6β-fluoro-17α,21-dihydroxy-pregna-1,4-diene-3,20-dione-17,21-diacetate (8g, $R_1=R_2$OCOCH$_3$, $R_3$=H, X=Y=Cl) was converted into 2,9α,11β-trichloro-6β-fluoro-17α,21-dihydroxy-pregna-1,4-diene-3,20-dione (8m, $R_1=R_2$=OH, $R_3$=H, X=Y=Cl).

IR(KBr) 3450 (broad), 1710, 1675, 1610 cm$^{-1}$.

Analysis: Calcd. for $C_{21}H_{24}Cl_3FO_4$ (percent): C 54.15; H 5.19; Cl 22.83; F 4.08. Found (percent): C 54.25; H 5.21; Cl 22.91; F 4.12.

EXAMPLE XXIX

Using the general procedure of Example XXV the 2,9α,11β-trichloro-6β-fluoro-17α,21-dihydroxy-16α-methyl-pregna-1,4-diene-3,20-dione-17,21-diacetate (8h, $R_1=R_2$=OCOCH$_3$, $R_3$=αCH$_3$, X=Y=Cl) was converted into 2,9α,11β-trichloro-6β-fluoro-17α,21-dihydroxy-16α-methyl-pregna-1,4-diene-3,20-dione (8n, $R_1=R_2$=OH, X=Y=Cl, $R_3$=αCH$_3$).

IR(KBr) 3460 (broad), 1710, 1675, 1610 cm$^{-1}$.

Analysis: Calcd. for $C_{22}H_{26}Cl_3FO_4$ (percent): C 55.07; H 5.46; Cl 22.17; F 3.96. Found (percent): C 55.13; H 5.42; Cl 22.18; F 3.95.

EXAMPLE XXX

Using the general procedure of Example XXV the 2,9α,11β-trichloro-6β-fluoro-17α,21-dihydroxy-16β-methyl-pregna-1,4-diene-3,20-dione-17,21-diacetate (8i, $R_1=R_2$=OCOCH$_3$, $R_3$=βCH$_3$, X=Y=Cl) was converted into 2,9α,11β-trichloro-6β-fluoro-17α,21-dihydroxy-16β-methyl-pregna-1,4-diene-3,20-dione (8o, $R_1=R_2$=OH, $R_3$=βCH$_3$, X=Y=Cl).

IR(KBr) 3450 (broad), 1712, 1672, 1610 cm$^{-1}$.

Analysis: Calcd. for $C_{22}H_{26}Cl_3FO_4$ (percent): C 55.07; H 5.46; Cl 22.17; F 3.96. Found (percent): C 55.18; H 5.52; Cl 22.23; F 3.98.

EXAMPLE XXXI 2.9 g. of 2-chloro-6β,9α-difluoro-11β,17α,21-trihydroxy-pregna-1,4-diene-3,20-dione (8j, $R_1=R_2$=OH, $R_3$=H, X=OH, Y=F) were dissolved in 29 ml. of pyridine containing 15 ml. of acetic anhydride and kept at room temperature for 12 hrs. Addition of ice water afforded a product which was extracted with chloroform. The chloroform solution was washed with water, HCl2N, 5% sodium bicarbonate solution and water. After drying (Na$_2$SO$_4$) and removal of the solvent in vacuo the residue was crystallized from acetone-hexane to give 1.7 g. of 2-chloro-6β,9α-difluoro-11β,17α,21-trihydroxy-pregna-1,4-diene-3,20-dione-21-acetate (8p, $R_1$=OCOCH$_3$, $R_2$=OH, X=OH, Y=F, $R_3$=H.

M.P. 225°-27° C.

$[\alpha]_D$+21° (C 1.0 in chloroform).

IR(CHCl$_3$) 3700, 3620, 1750, 1735, 1680, 1650, 1610.

Analysis: Calcd. for $C_{23}H_{27}ClF_2O_6$ (percent): C 58.42; H 5.75; Cl 7.50; F 8.03. Found (percent): C 58.60; H 5.80; Cl 7.50; F 8.02.

EXAMPLE XXXII

Using the general procedure of Example XXXI the 2-chloro-6β,9α-difluoro-11β,17α,21-trihydroxy-16α-methyl-pregna-1,4-diene-3,20-dione (8k, $R_1=R_2$=OH, $R_3$=αCH$_3$, X=OH, Y=F) was converted into 2-chloro-6β,9α-difluoro-11β,17α,21-trihydroxy-16α-methyl-pregna-1,4-diene-3,20-dione-21-acetate (8q, $R_1$=OCOCH$_3$, $R_2$=OH, $R_3$=αCH$_3$, X=OH, Y=F).

IR(CHCl$_3$) 3700, 3620, 1750, 1730, 1680, 1645, 1605.

Analysis: Calcd. for $C_{24}H_{29}ClF_2O_6$ (percent): C 59.20; H 6.00; Cl 7.28; F 7.80. Found (percent): C 59.32; H 6.02; Cl 7.35; F 7.83.

EXAMPLE XXXIII

Using the general procedure of Example XXXI the 2-chloro-6β,9α-difluoro-11β,17α,21-trihydroxy-16β-methyl-pregna-1,4-diene-3,20-dione (8l, $R_1=R_2$=OH, $R_3$=βCH$_3$, X=OH, Y=F) was converted into 2-chloro-6β,9α-difluoro-11β,17α,21-trihydroxy-16β-methyl-pregna-1,4-diene-3,20-dione-21-acetate (8r, $R_1$=OCOCH$_3$, $R_2$=OH, X=OH, Y=F, $R_3$=βCH$_3$).

IR(CHCl$_3$) 3705, 3620, 1745, 1730, 1680, 1645, 1605 cm$^{-1}$.

Analysis: Calcd. for $C_{24}H_{29}ClF_2O_6$ (percent): C 59.20; H 6.00; Cl 7.28; F 7.80. Found (percent): C 59.40; H 6.05; Cl 7.35; F 7.82.

EXAMPLE XXXIV

Using the general procedure of Example XXXI the 2,9α,11β-trichloro-6β-fluoro-17α,21-dihydroxy-pregna-1,4-diene-3,20-dione (8m, $R_1=R_2$=OH, $R_3$=H, X=Y=Cl) was converted into 2,9α,11β-trichloro-6β-fluoro-17α,21-dihydroxy-pregna-1,4-diene-3,20-dione-21-acetate (8s, $R_1$=OCOCH$_3$, $R_2$=OH, $R_3$=H, X=Y=Cl).

IR(CHCl$_3$) 3600 (broad), 1740, 1730, 1680, 1645, 1605, 1230 cm$^{-1}$.

Analysis: Calcd. for $C_{23}H_{26}Cl_3FO_5$ (percent): C 54.40; H 5.16; Cl 20.94; F 3.74. Found (percent): C 54.56; H 5.16; Cl 20.90; F 3.80.

EXAMPLE XXXV

Using the general procedure of Example XXXI the 2,9α,11β-trichloro-6β-fluoro-17α,21-dihydroxy-16α-methyl-pregna-1,4-diene-3,20-dione (8n, $R_1=R_2$=OH, $R_3$=αCH$_3$, X=Y=Cl) was converted into 2,9α,11β-trichloro-6β-fluoro-17α,21-dihydroxy-16α-methyl-pregna-1,4-diene-3,20-dione-21-acetate (8t, $R_1$=OCOCH$_3$, $R_2$=OH, $R_3$=αCH$_3$, X=Y=Cl).

IR(CHCl$_3$) 3600 (broad), 1742, 1730, 1680, 1640, 1605, 1230 cm$^{-1}$.

Analysis: Calcd. for $C_{24}H_{28}Cl_3FO_5$ (percent): C 55.24; H 5.41; Cl 20.38; F 3.64. Found (percent): C 55.32; H 5.43; Cl 20.42; F 3.68.

EXAMPLE XXXVI

Using the general procedure of Example XXXI the 2,9α,11β-trichloro-6β-fluoro-17α,21-dihydroxy-16β-methyl-pregna-1,4-diene-3,20-dione (8o, $R_1=R_2$=OH, $R_3=\beta CH_3$, X=Y=Cl) was converted into 2,9α,11β-trichloro-6β-fluoro-17α,21-dihydroxy-16β-methyl-pregna-1,4-diene-3,20-dione-21-acetate (8u, $R_1$=OCOCH$_3$, $R_2$=OH, $R_3=\beta CH_3$, X=Y=Cl).

IR(CHCl$_3$) 3610 (broad), 1740, 1728, 1675, 1645, 1610, 1235 cm$^{-1}$.

Analysis: Calcd. for $C_{24}H_{28}Cl_3FO_5$ (percent): C 55.24; H 5.41; Cl 20.38; F 3.64. Found (percent): C 55.20; H 5.53; Cl 20.47; F 3.62.

EXAMPLE XXXVII

Using the general procedure of Example XXXI the 2-chloro-6β,9α-difluoro-11β,17α,21-trihydroxy-pregna-1,4-diene-3,20-dione (8j, $R_1=R_2$=OH, $R_3$=H, X=OH, Y=F) was converted into 2-chloro-6β,9α-difluoro-11β,17α,21-trihydroxy-pregna-1,4-diene-3,20-dione-21-hemisuccinate (8v, $R_1$=OCOCH$_2$CH$_2$COOH, $R_2$=OH, $R_3$=H, X=OH, Y=F) which was crystallized from water.

M.P. 149°–152° C.

$[\alpha]_D^{20}$ +26° (C 1.0 in dioxane).

λmax (methanol) 244–5mμ (ε12600).

IR(KBr) 3500 (broad), 1730 (broad), 1670, 1640, 1610 cm$^{-1}$.

Analysis: Calcd. for $C_{25}H_{29}ClF_2O_8$ (percent): C 56.55; H 5.51; Cl 6.68; F, 7.16. Found (percent): C 56.81; H 5.55; Cl 6.72; F 7.12.

EXAMPLE XXXVIII

Using the general procedure of Example XXXI the 2-chloro-6β,9α-difluoro-11β,17α,21-trihydroxy-16α-methyl-pregna-1,4-diene-3,20-dione (8k, $R_1=R_2$=OH, $R_3=\alpha CH_3$, X=OH, Y=F) was converted into 2-chloro-6β,9α-difluoro-11β,17α,21-trihydroxy-16α-methyl-pregna-1,4-diene-3,20-dione-21-hemisuccinate (8w, $R_1$=OCOCH$_2$CH$_2$COOH, $R_2$=OH, $R_3=\alpha CH_3$, X=OH, Y=F) which was crystallized from water.

IR(KBr) 3500 (broad), 1725, 1675, 1640, 1610 cm$^{-1}$.

Analysis: Calcd. for $C_{26}H_{31}ClF_2O_8$ (percent): C 57.30; H 5.73; Cl 6.51; F 6.97. Found (percent): C 57.45; H 5.72; Cl 6.49; F 6.91.

EXAMPLE XXXIX

Using the general procedure of Example XXXI the 2-chloro-6β,9α-difluoro-11β,17α,21-trihydroxy-16β-methyl-pregna-1,4-diene-3,20-dione (8l, $R_1=R_2$=OH, $R_3=\beta CH_3$, X=OH, Y=F) was converted into 2-chloro-6β,9α-difluoro-11β,17α,21-trihydroxy-16β-methyl-pregna-1,4-diene-3,20-dione-21-hemisuccinate (8z, $R_1$=OCOCH$_2$CH$_2$COOH, $R_2$=OH, $R_3=\beta CH_3$, X=OH, Y=F) which was crystallized from water.

IR(KBr) 3500 (broad), 1730, 1680, 1640, 1610 cm$^{-1}$.

Analysis: Calcd. for $C_{26}H_{31}ClF_2O_8$ (percent): C 57.30; H 5.73; Cl 6.51; F 6.97. Found (percent): C 57.45; H 5.81; Cl 6.57; F 7.02.

EXAMPLE XL 0.1 N NaOH solution was slowly added to a stirred solution of 1.9 g. of 2-chloro-6β,9α-difluoro-11β,17α,21-trihydroxy-pregna-1,4-diene-3,20-dione-21-hemisuccinate in 50 ml. of acetone until the pH rose to 7.4. During the addition of NaOH solution, 100 ml. of water were also added. The solution was concentrated at 25° C. under vacuum to remove the acetone. The resulting aqueous solution was filtered and freeze-dried to give 1.9 g. of 2-chloro-6β,9α-difluoro-11β,17α,21-trihydroxy-pregna-1,4-diene-3,20-dione-21-hemisuccinate sodium salt (8 aa, $R_1$=OCOCH$_2$CH$_2$COONa, $R_2$=OH, $R_3$=H, X=OH, Y=F).

$[\alpha]_D^{20}$ +33° (C 0.5 in water).

λmax (methanol) 245 mμ (ε11500).

IR(KBr) 3470 (broad), 1725, 1675, 1645, 1580 (broad).

EXAMPLE XLI

Using the general procedure of Example XL the 2-chloro-6β,9α-difluoro-11β,17α,21-trihydroxy-16α-methyl-pregna-1,4-diene-3,20-dione-21-hemisuccinate (8w, $R_1$=OCOCH$_2$CH$_2$COOH, $R_2$=OH, $R_3=\alpha CH_3$, X=OH, Y=F) was converted into 2-chloro-6β,9α-difluoro-11β,17α,21-trihydroxy-16α-methyl-pregna-1,4-diene-3,20-dione-21-hemisuccinate sodium salt (8 ab, $R_1$=OCOCH$_2$CH$_2$COONa, $R_2$=OH, $R_3=\alpha CH_3$, X=OH, Y=F).

IR(KBr) 3480 (broad), 1670, 1640, 1580 (broad).

EXAMPLE XLII

Using the general procedure of Example XL the 2-chloro-6β,9α-difluoro-11β,17α,21-trihydroxy-16β-methyl-pregna-1,4-diene-3,20-dione-21-hemisuccinate (8z, $R_1$=OCOCH$_2$CH$_2$COOH, $R_2$=OH, $R_3=\beta CH_3$, X=OH, Y=F) was converted into 2-chloro-6β,9α-difluoro-11β,17α,21-trihydroxy-16β-methyl-pregna-1,4-diene-3,20-dione-21-hemisuccinate sodium salt (8 ac, $R_1$=OCOCH$_2$CH$_2$COONa, $R_2$=OH, $R_3=\beta CH_3$, X=OH, Y=F).

IR(KBr) 3490 (broad), 1675, 1645, 1580 (broad).

EXAMPLE XLIII

A mixture of 5 g. of 2-chloro-6β,9α-difluoro-11β,17α,21-trihydroxy-pregna-1,4-diene-3,20-dione (8j, $R_1=R_2$=OH, $R_3$=H, X=OH, Y=F), 5 ml. of methylorthovalerate and 0.020 g. of p-toluenesulfonic acid in 15 ml. of dimethylformamide was maintained for 4 hrs. under nitrogen at 115° C. Then the mixture was neutralized by pyridine and concentrated under vacuum to dryness. Purification by column chromatography on FLORISIL (Registered Trade Mark) (ratio 1:150) with benzene-chloroform (1:1) as eluant, gave 4 g. of 2-chloro-6β,9α-difluoro-11β,17α,21-trihydroxy-pregna-1,4-diene-3,20-dione-17,21-(1'-methoxy)-n-pentylidenedioxy which, without further purification, was suspended in 25 ml. of methanol and 3 ml. of 1 N hydrochloric acid aqueous solution, heated on water bath at 40°-50° C.

After complete solubilization of the product, the mixture was concentrated under vacuum. The insoluble product was filtered off, washed with water and then dried.

The 2-chloro-6β,9α-difluoro-11β,17α,21-trihydroxy-pregna-1,4-diene-3,20-dione-17-valerate (8 ad, $R_1$=OH, $R_2$=OCO(CH$_2$)$_3$CH$_3$, $R_3$=H, X=OH, Y=F) thus obtained was crystallized from acetone-n-hexane and characterized by IR(KBr) 3500 (broad), 1730, 1710, 1675, 1645, 1600 cm$^{-1}$.

Analysis: Calcd. for $C_{26}H_{33}ClF_2O_6$ (percent): C 60.64; H 6.46; Cl 6.88; F 7.38. Found (percent): C 60.70; H 6.45; Cl 6.88; F 7.35.

EXAMPLE XLIV

Using the general procedure of Example XLIII the 2-chloro-6β,9α-difluoro-11β,17α,21-trihydroxy-pregna-1,4-diene-3,20-dione (8j, $R_1=R_2$=OH, $R_3$=H, X=OH, Y=F) was converted into 2-chloro-6β,9α-difluoro-11β,17α,21-trihydroxy-pregna-1,4-diene-3,20- dione-17-acetate (8 ae, R$_1$=OH, R$_2$=OCOCH$_3$, R$_3$=H, X=OH, Y=F) by reaction with ethylorthoacetate followed by hydrolysis of the resulting 17,21-orthoacetate.

IR(KBr) 3490 (broad), 1730, 1710, 1670, 1645, 1600 cm$^{-1}$.

Analysis: Calcd. for C$_{23}$H$_{27}$ClF$_2$O$_6$ (percent): C 58.42; H 5.75; Cl 7.50; F 8.03. Found (percent): C 58.52; H 5.80; Cl 7.50; F 8.00.

EXAMPLE XLV

Using the general procedure of Example XLIII the 2-chloro-6β,9α-difluoro-11β,17α,21-trihydroxy-16α-methyl-pregna-1,4-diene-3,20-dione (8k, R$_1$=R$_2$=OH, R$_3$=αCH$_3$, X=OH, Y=F) was converted into 2-chloro-6β,9α-difluoro-11β,17α,21-trihydroxy-16α-methyl-pregna-1,4-diene-3,20-dione-17-acetate (8 af, R$_1$=OH, R$_2$=OCOCH$_3$, X=OH, Y=F, R$_3$=βCH$_3$) by reaction with ethylorthoacetate followed by hydrolysis of the resulting 17,21-orthoacetate.

IR(KBr) 3500 (broad), 1735 (broad), 1675, 1645, 1605 cm$^{-1}$.

Analysis: Calcd. for C$_{24}$H$_{29}$ClF$_2$O$_6$ (percent): C 59.20; H 6.00; Cl 7.28; F 7.80. Found (percent): C 59.29; H 6.02; Cl 7.31; F 7.78.

EXAMPLE XLVI

Using the general procedure of Example XLIII the 2-chloro-6β,9α-difluoro-11β,17α,21-trihydroxy-16β-methyl-pregna-1,4-diene-3,20-dione (8l, R$_1$=R$_2$=OH, R$_3$=βCH$_3$, X=OH, Y=F) was converted into 2-chloro-6β,9α-difluoro-11β,17α,21-trihydroxy-16β-methyl-pregna-1,4-diene-3,20-dione-17-acetate (8 ag, R$_1$=OH, R$_2$=OCOCH$_3$, R$_3$=βCH$_3$, X=OH, Y=F) by reaction with ethylorthoacetate followed by hydrolysis of the resulting 17,21-orthoacetate.

IR(KBr) 3500 (broad), 1730 (broad), 1672, 1645, 1600 cm$^{-1}$.

Analysis: Calcd. for C$_{24}$H$_{29}$ClF$_2$O$_6$ (percent): C 59.20; H 6.00; Cl 7.28; F 7.80. Found (percent): C 59.15; H 5.98; Cl 7.35; F 7.78.

EXAMPLE XLVII

Using the general procedure of Example XLIII the 2,9α,11β-trichloro-6β-fluoro-17α,21-dihydroxy-pregna-1,4-diene-3,20-dione (8m, R$_1$=R$_2$=OH, R$_3$=H, X=Y=Cl) was converted into 2,9α,11β-trichloro-6β-fluoro-17α,21-dihydroxy-pregna-1,4-diene-3,20-dione-17-acetate (8 ah, R$_1$=OH, R$_2$=OCOCH$_3$, R$_3$=H, X=Y=Cl) by reaction with ethylorthoacetate followed by acid hydrolysis of the resulting 17,21-orthoacetate.

IR(KBr) 3500 (broad), 1730, 1715, 1672, 1645, 1605, 1230 cm$^{-1}$.

Analysis: Calcd. for C$_{23}$H$_{26}$Cl$_3$FO$_5$ (percent): C 54.40; H 5.16; Cl 20.94; F 3.74. Found (percent): C 54.60; H 5.12; Cl 20.92; F 3.76.

EXAMPLE XLVIII

Using the general procedure of Example XLIII the 2,9α,11β-trichloro-6β-fluoro-17α,21-dihydroxy-16α-methyl-pregna-1,4-diene-3,20-dione (8n, R$_1$=R$_2$=OH, R$_3$=αCH$_3$, X=Y=Cl) was converted into 2,9α,11β-trichloro-6β-fluoro-17α,21-dihydroxy-16α-methyl-pregna-1,4-diene-3,20-dione-17-acetate (8 ai, R$_1$=OH, R$_2$=OCOCH$_3$, R$_3$=αCH$_3$, X=Y=Cl) by reaction with ethylorthoacetate followed by acid hydrolysis of the resulting 17,21-orthoacetate.

IR(KBr) 3500 (broad), 1728, 1715, 1670, 1645, 1600, 1230 cm$^{-1}$.

Analysis: Calcd. for C$_{24}$H$_{28}$Cl$_3$FO$_5$ (percent): C 55.24; H 5.41; Cl 20.38; F 3.64. Found (percent): C 55.32; H 5.50; Cl 20.36; F 3.64.

EXAMPLE XLIX

Using the general procedure of Example XLIII the 2,9α,11β-trichloro-6β-fluoro-17α,21-dihydroxy-16β-methyl-pregna-1,4-diene-3,20-dione (8o, R$_1$=R$_2$=OH, R$_3$=βCH$_3$, X=Y=Cl) was converted into 2,9α,11β-trichloro-6β-fluoro-17α,21-dihydroxy-16β-methyl-pregna-1,4-diene-3,20-dione-17-acetate (8 aj, R$_1$=OH, R$_2$=OCOCH$_3$, R$_3$=βCH$_3$, X=Y=Cl) by reaction with ethylorthoacetate followed by acid hydrolysis of the resulting 17,21-orthoacetate.

IR(KBr) 3500 (broad), 1730, 1712, 1673, 1645, 1605, 1230 cm$^{-1}$.

Analysis: Calcd. for C$_{24}$H$_{28}$Cl$_3$FO$_5$ (percent): C 55.24; H 5.41; Cl 20.38; F 3.64. Found (percent): C 55.20; H 5.40; Cl 20.35; F 3.62.

EXAMPLE L

A solution of 6 g. of 2-chloro-6β,9α-difluoro-11β,17α,21-trihydroxy-pregna-1,4-diene-3,20-dione (8j, X=OH, Y=F, R$_1$=R$_2$=OH, R$_3$=H) in 12 ml. of dimethylformamide and 40 ml. of 2,2-dimethoxypropane with 0.030 g. of p-toluenesulfonic acid was heated for 5 hrs. at 115° C.

The reaction mixture was cooled, poured in 10% sodium bicarbonate aqueous solution and chloroform. The chloroform solution was then washed with water, dried and evaporated to a residue which by crystallization from acetone-hexane gave 5 g. of 2-chloro-6β,9α-difluoro-11β,17α,21-trihydroxy-pregna-1,4-diene-3,20-dione-17,21-acetonide (8 ak).

IR(KBr) 3450 (broad), 1720, 1672, 1645, 1605 cm$^{-1}$.

Analysis: Calcd. for C$_{24}$H$_{29}$ClF$_2$O$_5$ (percent): C 61.21; H 6.21; Cl 7.53; F 8.07. Found (percent): C 61.27; H 6.22; Cl 7.55; F 8.09.

EXAMPLE LI Using the general procedure of Example L the 2-chloro-6β,9α-difluoro-11β,17α,21-trihydroxy-16α-methyl-pregna-1,4-diene-3,20-dione (8k, X=OH, Y=F, R$_1$=R$_2$=OH, R$_3$=αCH$_3$) was converted into 2-chloro-6β,9α-difluoro-11β,17α,21-trihydroxy-16α-methyl-pregna-1,4-diene-3,20-dione-17,21-acetonide (8 al) characterized by IR(KBr) 3480 (broad), 1725, 1670, 1645, 1610 cm$^{-1}$.

Analysis: Calcd. for C$_{25}$H$_{31}$ClF$_2$O$_5$ (percent): C 61.92; H 6.44; Cl 7.31; F 7.83. Found (percent): C 62.07; H 6.39; Cl 7.35; F 7.85.

EXAMPLE LII

Using the general procedure of Example L the 2-chloro-6β,9α-difluoro-11β,17α,21-trihydroxy-16β-methyl-pregna-1,4-diene-3,20-dione (8l, R$_1$=R$_2$=OH, R$_3$=βCH$_3$, X=OH, Y=F) was converted into 2-chloro-6β,9α-difluoro-11β,17α,21-trihydroxy-16β-methyl-pregna-1,4-diene-3,20-dione-17,21-acetonide (8 am), characterized by IR(KBr) 3500 (broad), 1730, 1675, 1645, 1605 cm$^{-1}$.

Analysis: Calcd. for C$_{25}$H$_{31}$ClF$_2$O$_5$ (percent): C 61.92; H 6.44; Cl 7.31; F 7.83. Found (percent): C 61.98; H 6.44; Cl 7.36; F 7.85.

EXAMPLE LIII

A mixture of 10 g. of 2-chloro-6β,9α-difluoro-11β,17α,21-trihydroxy-pregna-1,4-diene-3,20-dione-17,21-diacetate (8a, X=OH, Y=F, R₁=R₂=OCOCH₃, R₃=H), in 100 ml. of dimethylformamide and 50 g. of anhydrous potassium acetate was refluxed at 120° C. under nitrogen for 0.5 hr. The reaction mixture was then cooled and poured into cold water.

The precipitate was filtered off, washed with water, dried. Crystallization of the residue from acetone-hexane gave 7.5 g. of 2-chloro-6β,9α-difluoro-11β,21-dihydroxy-pregna-1,4,16-triene-3,20-dione-21-acetate (9a, X=OH, Y=F, R₁=OCOCH₃) characterized by IR(KBr) 3520, 1730, 1680, 1645, 1605, 1590, 1220 cm$^{-1}$.

Analysis: Calcd. for $C_{23}H_{25}ClF_2O_5$ (percent): C 60.73; H 5.54; Cl 7.79; F 8.35. Found (percent): C 60.83; H 5.60; Cl 7.82; F 8.37.

EXAMPLE LIV

A solution of potassium permanganate (5 g.) in acetone (100 ml.) and water (30 ml.) was added, in one portion, at −5° C. to a solution of 7 g. of 2-chloro-6β,9α-difluoro-11β,21-dihydroxy-pregna-1,4,16-triene-3,20-dione-21-acetate (9a, X=OH, Y=F, R₁=OCOCH₃) in acetone (200 ml.) and formic acid (2.5 ml.).

The reaction mixture was stirred for 5 minutes at −5° C. and then 50 ml. of 10% Na₂SO₃ aqueous solution were added. The mixture was filtered through Celite (Registered Trade Mark) and the filtrate concentrated in vacuo and poured into cold water.

The solid filtered after crystallization from acetone-hexane yielded 6.5 g. of 2-chloro-6β,9α-difluoro-11β,16α,17α,21-tetrahydroxy-pregna-1,4-diene-3,20-dione-21-acetate (10a, X=OH, Y=F, R₁=OCOCH₃) characterized by IR(KBr) 3450 (broad), 1745, 1730, 1675, 1645, 1605, 1230 cm$^{-1}$.

Analysis: Calcd. for $C_{23}H_{27}ClF_2O_7$ (percent): C 56.50; H 5.57; Cl 7.25; F 7.77. Found (percent): C 56.56; H 5.61; Cl 7.27; F 7.80.

EXAMPLE LV

Using the general procedure of Example XXV the 2-chloro-6β,9α-difluoro-11β,16α,17α,21-tetrahydroxy-pregna-1,4-diene-3,20-dione-21-acetate (10a, X=OH, Y=F, R₁=OCOCH₃) was converted into 2-chloro-6β,9α-difluoro-11β,16α,17α,21-tetrahydroxy-pregna-1,4-diene-3,20-dione (10b, X=OH, Y=F, R₁=OH) characterized by IR(KBr) 3480 (broad), 1715, 1670, 1645, 1605 cm$^{-1}$.

Analysis: Calcd. for $C_{21}H_{25}ClF_2O_6$ (percent): C 56.44; H 5.64; Cl 7.93; F 8.50. Found (percent): C 56.31; H 5.62; Cl 7.98; F 8.45.

EXAMPLE LVI 2.5 ml. of 70% perchloric acid were added under stirring at 15° C. to a suspension of 10 g. of 2-chloro-6β,9α-difluoro-11β,16α,17α,21-tetrahydroxy-pregna-1,4-diene-3,20-dione-21-acetate (10a, X=OH, Y=F, R₁=OCOCH₃) in 400 ml. of acetone. The solution was stirred at 15° C. for 50 minutes and 5 g. of sodium bicarbonate were added. The mixture was stirred for 10 minutes and then filtered.

The acetone solution was evaporated to dryness in vacuo at 60° C.

The solid residue was crystallized from ethylacetate-light petroleum giving 6 g. of pure 2-chloro-6β,9α-difluoro-11β,16α,17α,21-tetrahydroxy-pregna-1,4-diene-3,20-dione-21-acetate-16,17-acetonide (11a, X=OH, Y=F, R₁=OCOCH₃, R₄=R₅=CH₃) characterized by IR(KBr) 3560, 3480, 3420, 1755, 1730, 1670, 1645, 1605, 1230 cm$^{-1}$.

Analysis: Calcd. for $C_{26}H_{31}ClF_2O_7$ (percent): C 59.04; H 5.91; Cl 6.70 F 7.18. Found (percent): C 59.15; H 5.88; Cl 6.72; F 7.15.

EXAMPLE LVII

Using the general procedure of Example LVI the 2-chloro-6β,9α-difluoro-11β,16α,17α,21-tetrahydroxy-pregna-1,4-diene-3,20-dione (10b, X=OH, Y=F, R₁=OH) was converted into 2-chloro-6β,9α-difluoro-11β,16α,17α,21-tetrahydroxy-pregna-1,4-diene-3,20-dione-16,17-acetonide (11b, X=OH, Y=F, R₁=OH, R₄=R₅=CH₃).

IR(KBr) 3500, 3280, 1725, 1670, 1645, 1600 cm$^{-1}$.

Analysis: Calcd. for $C_{24}H_{29}ClF_2O_6$ (percent): C 59.20; H 6.00; Cl 7.28; F 7.80. Found (percent): C 59.32; H 6.09; Cl 7.31; F 7.78.

EXAMPLE LVIII 5 ml. of acetic anhydride were dropwise added to a mixture of 50 ml. of pyridine and 10 g. of 2-chloro-6β,9α-difluoro-11β,16α,17α,21-tetrahydroxy-pregna-1,4-diene-3,20-dione-21-acetate (10a, X=OH, Y=F, R₁=OCOCH₃). The mixture was kept at room temperature for 1.5 hr. and then poured under vigorous stirring into 1500 ml. of cold water.

After about 0.5 hr. the solid was collected by filtration, washed thoroughly with cold water, dried to a constant weight, giving about 9 g. of 2-chloro-6β,9α-difluoro-11β,16α,17α 21-tetrahydroxy-pregna-1,4-diene-3,20-dione-16,21-diacetate (12a, X=OH, Y=F, R₁=R₃=OCOCH₃).

IR(KBr) 3570, 3500 (broad), 1760, 1740 (broad), 1675, 1645, 1605, 1225 cm$^{-1}$.

Analysis: Calcd. for $C_{25}H_{29}ClF_2O_8$ (percent): C 56.55; H 5.51; Cl 6.68; F 7.16. Found (percent): C 56.61; H 5.51; Cl 6.72; F 7.16.

We claim:

1. A compound having the formula:

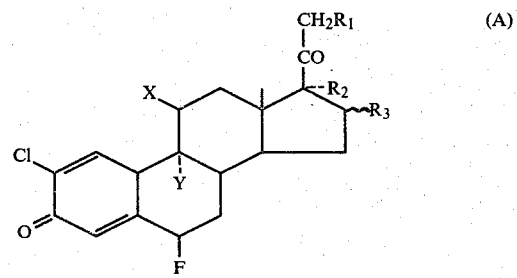

wherein X is Br or Cl, Y is Br, Cl or F R₁ is OQ, R₂ is OQ and R₃ is H, or αOQ, and Q, which may be the same or different, is H or acyl radicals, or OQ in the 16,17 or in the 17,21 positions may together form a cyclic ketal, cyclic acetal or cyclic alkyl orthoester, and pharmaceutically acceptable salts and esters of those compounds wherein at least one radical Q is a polycarboxylic or an inorganic acid radical.

2. The compound according to claim 1, in which Q in at least one of the 16, 17 or 21 positions represents an acyl radical.

3. The compound according to claim 1 in which OQ in the 21 position forms an inorganic ester with their salts.

4. A compound having the formula:

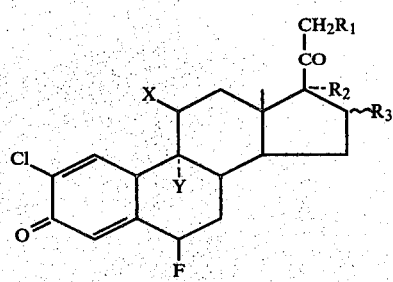

wherein X is Br or Cl, Y is Br, Cl or F, $R_1$ is OQ in the 21 position and forms an alkyl orthoester, $R_2$ is OQ and $R_3$ is H, $\alpha$OQ, $\alpha$CH$_3$ or $\beta$CH$_3$, and Q, which may be the same or different, is H, or acyl radicals, or OQ in the 16, 17 or in the 17,21 positions may together form a cyclic alkyl orthoester, and pharmaceutically acceptable salts and esters of those compounds wherein at least one radical Q is a polycarboxylic or an inorganic acid radical.

5. A pharmaceutical composition comprising an active compound according to claim 4 together with a pharmaceutically acceptable carrier.

6. A method of combatting inflammation in a patient comprising applying a compound according to claim 4 to the patient topically or or systemically in a non-toxic pharmaceutically effective amount.

7. A compound having the formula:

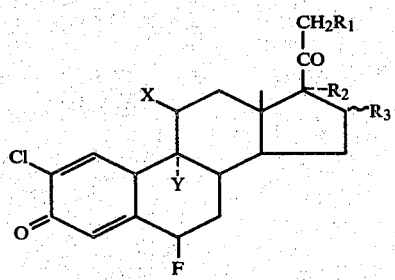

wherein X is Br, Cl or OQ, Y is Br, Cl, F or H, $R_1$ is OQ, $R_2$ is OQ and $R_3$ is $\alpha$OQ, and Q in the 16, 17 and 21 positions represents H and in the 11 position represents H or an acyl radical and pharmaceutically acceptable salts and esters of those compounds wherein Q in the 11 position represents a polycarboxylic or an inorganic acid radical.

8. The compound according to claim 7 wherein X is OH.

9. The compound according to claim 7 wherein Y is F.

10. The compound according to claim 7 wherein X is Br or Cl and Y is Br, Cl or F.

11. The compound according to claim 7 wherein X is OH and Y is Br, Cl or F.

12. The compound according to claim 7 wherein Y is Br.

13. A pharmaceutical composition comprising an active compound according to claim 7 together with a pharmaceutically acceptable carrier.

14. A method of combatting inflammation in a patient comprising applying a compound according to claim 7 to the patient topically or systemically in a non-toxic pharmaceutically effective amount.

15. The compound of claim 1 which is 2,9$\alpha$,11$\beta$-trichloro-6$\beta$-fluoro-17$\alpha$,21-dihydroxy-pregna-1,4-diene-3,20-dione-17,21-diacetate.

16. The compound of claim 22 which is 2,9$\alpha$,11$\beta$-trichloro-6$\beta$-fluoro-17$\alpha$,21-dihydroxy-pregna-1,4-diene-3,20-dione.

17. The compound of claim 1 which is 2,9$\alpha$,11$\beta$-trichloro-6$\beta$-fluoro-17$\alpha$,21-dihydroxy-pregna-1,4-diene-3,20-dione-21-acetate.

18. The compound of claim 1 which is 2,9$\alpha$,11$\beta$-trichloro-6$\beta$-fluoro-17$\alpha$,21-dihydroxy-pregna-1,4-diene-3,20-dione-17-acetate.

19. The compound of claim 1 which is 2-chloro-6$\beta$,9$\alpha$-difluoro-11$\beta$,16$\alpha$,17$\alpha$,21-tetrahydroxy-pregna-1,4-diene-3,20-dione-21-acetate.

20. The compound of claim 1 which is 2-chloro-6$\beta$,9$\alpha$-difluoro-11$\beta$,16$\alpha$,17$\alpha$,21-tetrahydroxy-pregna-1,4-diene-3,20-dione.

21. The compound of claim 1 which is 2-chloro-6$\beta$,9$\alpha$-difluoro-11$\beta$,16$\alpha$,17$\alpha$,21-tetrahydroxy-pregna-1,4-diene-3,20-dione-16,17-acetonide-21-acetate.

22. The compound of claim 1 which is 2-chloro-6$\beta$,9$\alpha$-difluoro-11$\beta$,16$\alpha$,17$\alpha$,21-tetrahydroxy-pregna-1,4-diene-3,20-dione-16,17-acetonide.

23. The compound of claim 1 which is 2-chloro-6$\beta$,9$\alpha$-difluoro-11$\beta$,16$\alpha$,17$\alpha$,21-tetrahydroxy-pregna-1,4-diene-3,20-dione-16,21-diacetate.

* * * * *

UNITED STATES PATENT AND TRADEMARK OFFICE
CERTIFICATE OF CORRECTION

PATENT NO. : 4,275,061
DATED : June 23, 1981
INVENTOR(S) : Mario Riva, Luciane Toscano It is certified that error appears in the above—identified patent and that said Letters Patent is hereby corrected as shown below:

Column 7, line 3 "55799/74" should read "55748/74"

Column 7, line 42, "Sa" should read "8a"

Column 7, line 46, "(9α" should read "(9a"

Column 7, line 51, "(10α" should read "(10a"

Signed and Sealed this

Seventh Day of September 1982

[SEAL]

Attest:

GERALD J. MOSSINGHOFF

Attesting Officer

Commissioner of Patents and Trademarks